(12) United States Patent
Schweitzer et al.

(10) Patent No.: US 8,112,248 B2
(45) Date of Patent: Feb. 7, 2012

(54) FORENSIC INTEGRATED SEARCH TECHNOLOGY WITH INSTRUMENT WEIGHT FACTOR DETERMINATION

(75) Inventors: Robert Schweitzer, Pittsburgh, PA (US); Patrick J. Treado, Pittsburgh, PA (US); Jason Neiss, Pittsburgh, PA (US)

(73) Assignee: ChemImage Corp., Pittsburgh, PA (US)

( * ) Notice: Subject to any disclaimer, the term of this patent is extended or adjusted under 35 U.S.C. 154(b) by 1052 days.

(21) Appl. No.: 12/017,445

(22) Filed: Jan. 22, 2008

(65) Prior Publication Data
US 2008/0300826 A1 Dec. 4, 2008

Related U.S. Application Data

(63) Continuation-in-part of application No. 11/450,138, filed on Jun. 9, 2006.

(60) Provisional application No. 60/688,812, filed on Jun. 9, 2005, provisional application No. 60/711,593, filed on Aug. 26, 2005, provisional application No. 60/881,886, filed on Jan. 23, 2007.

(51) Int. Cl.
G06F 17/18 (2006.01)
G01N 31/00 (2006.01)

(52) U.S. Cl. .............................. 702/181; 702/31; 702/32

(58) Field of Classification Search .................... 702/22, 702/27, 28, 30–32, 85, 104, 181; 436/43; 25/339.09, 252.1; 707/600, 601
See application file for complete search history.

(56) References Cited

U.S. PATENT DOCUMENTS

| | | | |
|---|---|---|---|
| 5,446,681 A | 8/1995 | Gethner | |
| 6,553,334 B2 | 4/2003 | Gross et al. | |
| 6,609,086 B1 | 8/2003 | Bao et al. | |
| 6,917,423 B2 | 7/2005 | Gardner | |
| 6,950,184 B2 | 9/2005 | Stewart | |
| 7,428,045 B2 | 9/2008 | Stewart | |

(Continued)

FOREIGN PATENT DOCUMENTS
WO 2004038602 5/2004
(Continued)

OTHER PUBLICATIONS

PCT International Search Report from ISA/US in a related application mailed on Feb. 29, 2008.

(Continued)

*Primary Examiner* — Manuel L Barbee
(74) *Attorney, Agent, or Firm* — Kristin Biedinger (57) ABSTRACT

A system and method to search spectral databases and to identify unknown materials from multiple spectroscopic data in the databases. The methodology may be substantially automated and is configurable to determine weights to be accorded to spectroscopic data from different spectroscopic data generating instruments for improved identification of unknown materials. Library spectra from known materials are divided into training and validation sets. Initial, instrument-specific weighting factors are determined using a weight grid or weight scale. The training and validation spectra are weighted with the weighting factors and indicator probabilities for various sets of "coarse" weighting factors are determined through an iterative process. The finally-selected set of coarse weighting factors is further "fine tuned" using a weight grid with finer values of weights. The instrument-specific finer weight values may be applied to test data sets (or spectra) of an unknown material as well as to the library spectra from corresponding spectroscopic instruments. Instrument-specific weights for each class of samples may also be computed for additional customization and accuracy.

20 Claims, 5 Drawing Sheets

U.S. PATENT DOCUMENTS

| | | |
|---|---|---|
| 7,623,232 B2 | 11/2009 | Stewart |
| 2002/0183602 A1 | 12/2002 | Wenzel et al. |
| 2004/0073120 A1 | 4/2004 | Motz |
| 2004/0143402 A1* | 7/2004 | Colinge et al. ............ 702/19 |
| 2004/0162685 A1 | 8/2004 | Gross et al. |
| 2005/0065732 A1 | 3/2005 | Tilton |
| 2005/0143936 A1 | 6/2005 | Laughlin |
| 2007/0192035 A1 | 8/2007 | Schweitzer |
| 2008/0300826 A1 | 12/2008 | Schweitzer |
| 2009/0012723 A1 | 1/2009 | Treado |
| 2009/0163369 A1 | 6/2009 | Treado |

FOREIGN PATENT DOCUMENTS

| | | |
|---|---|---|
| WO | 2006/035806 | 12/2006 |
| WO | PCT/US2006/022618 | 12/2006 |

OTHER PUBLICATIONS

Osamu Yamamoto et al, An Integrated Spectral Data Base System Including IR. MS, 1H-NMR, 13C-NMR, ESR and Raman Spectra, Analytical Sciences (online), vol. 4, Jun. 1998 (Jun. 1988) pp. 233-239, XP002534313.

Masui H et al, Spectra: A Spectral Information Management System Featuring A Novel Combined Search Function, Journal of Chemical Information and Computer Sciences ACS, USA, vol. 36, No. 2, Mar. 1996 pp. 294-298, XP002534314.

K. Tanabe et al, Cosmos-Combined Search System for Molecular Spectra, Computer Enhanced Spectroscopy, vol. 2, No. 3, 1984, pp. 97-99. XP008108808, vol. 2, No. 3, Jul. 2000 pp. 1-7, XP008107468.

Ward, Dennis, "Use of an XRay Spectral Database in Forensic Science," Forensic Science Communications (online) vol. 2, No. 3, Jul. 2000 pp. 1-7, XP0081087468.

Sparkman, David, "Evaluating Electron Ionization Mass Spectral Library Search Results," Elsevier Science Inc, US, vol. 7, No. 4, Apr. 1, 1996, pp. 313-318, XP00472392.

Scweitzer, et al, "The Role of Chemometrics in Chemical Image Analysis," North American Chapter of International Chemometric Society, Newsletter #21, Oct. 2000, pp. 14-21.

Osamu Yamamoto et al, An Integrated Spectral Data Base System Including IR, MS, 1H-NMR, 13C-NMR, ESR and Raman Spectra, Analytical Sciences [online], vol. 4, Jun. 1988, pp. 233-239, XP002534313.

Masui H et al, Spectra: A Spectral Information Management System Featuring A Novel Combined Search Function, Journal of Chemical Information and Computer Sciences ACS USA, vol. 36, No. 2, Mar. 1996, pp. 294-298, XP002534314.

K. Tanabe et al, Cosmos-Combined Search System for Molecuiar Spectra, Computer Enhanced Spectroscopy, vol. 2, No. 3, 1984, pages 97-99, XP008107708.

Dennis Ward, Use of an X-Ray Spectral Database in Forensic Science, Forensic Science Communications [online], vol. 2, No. 3, Jul. 2000, pp. 1-7, XP008107468.

David Sparkman, Evaluating Electron Ionization Mass Spectral Library Search Results, Elsevier Science Inc, US, vol. 7, No. 4, Apr. 1, 1996, pp. 313-318, XP004720392.

* cited by examiner

FORENSIC INTEGRATED SEARCH TECHNOLOGY WITH INSTRUMENT WEIGHT FACTOR DETERMINATION

RELATED APPLICATIONS

This application is a continuation-in-part of pending U.S. patent application Ser. No. 11/450,138, titled "Forensic Integrated Search Technology" and filed on Jun. 9, 2006, which, in turn, claims the priority benefits of U.S. Provisional Application No. 60/688,812, filed on Jun. 9, 2005 and titled "Forensic Integrated Search Technology," and U.S. Provisional Application No. 60/711,593, filed on Aug. 26, 2005 and titled "Forensic Integrated Search Technology," the disclosures of all of these applications are incorporated herein by reference in their entireties. This application further claims priority benefit under 35 U.S.C. §119(e) of the U.S. Provisional Application No. 60/881,886, titled "Forensic Integrated Search Technology," and filed on Jan. 23, 2007, the disclosure of which is incorporated herein by reference in its entirety.

FIELD OF DISCLOSURE

This application generally relates to systems and methods for searching spectral databases and identifying unknown materials, and more particularly to an iterative weight grid-based methodology for determination of optimal operating set of weighting factors for spectroscopic data generating instruments.

BACKGROUND

The challenge of integrating multiple data types into a comprehensive database searching algorithm has yet to be adequately solved. Existing data fusion and database searching algorithms used in the spectroscopic community suffer from key disadvantages. Most notably, competing methods such as interactive searching are not scalable, and are at best semi-automated, requiring significant user interaction. For instance, the BioRAD KnowItAll® software claims an interactive searching approach that supports searching of up to three different types of spectral data using the search strategy most appropriate to each data type. Results are displayed in a scatter plot format, requiring visual interpretation (from a human operator) and restricting the scalability of the technique. Also, this method does not account for mixture component searches. Data Fusion Then Search (DFTS) is an automated approach that combines the data from all sources into a derived feature vector and then performs a search on that combined data. The data is typically transformed using a multivariate data reduction technique, such as Principal Component Analysis, to eliminate redundancy across data and to accentuate the meaningful features. This technique is also susceptible to poor results for mixtures, and it has limited capacity for user control of weighting factors.

Therefore, it is desirable to devise a system and method that allows users to identify unknown materials with multiple spectroscopic data and that is configurable to determine weights to be accorded to spectroscopic data from different spectroscopic data generating instruments for improved identification of unknown materials.

SUMMARY

The present disclosure provides for a system and method to search spectral databases and to identify unknown materials. A library having a plurality of sublibraries is provided wherein each sublibrary contains a plurality of reference data sets generated by a corresponding one of a plurality of spectroscopic data generating instruments associated with the sublibrary. Each reference data set characterizes a corresponding known material. A plurality of test data sets is provided that is characteristic of an unknown material, wherein each test data set is generated by one or more of the plurality of spectroscopic data generating instruments. For each test data set, each sublibrary is searched where the sublibrary is associated with the spectroscopic data generating instrument used to generate the test data set. A corresponding set of scores for each searched sublibrary is produced, wherein each score in the set of scores indicates a likelihood of a match between one of the plurality of reference data sets in the searched sublibrary and the test data set. A set of relative probability values is calculated for each searched sublibrary based on the set of scores for each searched sublibrary. All relative probability values for each searched sublibrary are fused producing a set of final probability values that are used in determining whether the unknown material is represented through a known material characterized in the library. A highest final probability value is selected from the set of final probability values and compared to a minimum confidence value. The known material represented in the libraries having the highest final probability value is reported, if the highest final probability value is greater than or equal to the minimum confidence value.

In another embodiment, if a highest final probability value is less than a minimum confidence value, the unknown material is treated as a mixture of known materials.

In one embodiment, the spectroscopic data generating instrument comprises one or more of the following: a Raman spectrometer; a mid-infrared spectrometer; an x-ray diffractometer; an energy dispersive x-ray analyzer; and a mass spectrometer. The reference data set comprises one or more of the following a Raman spectrum, a mid-infrared spectrum, an x-ray diffraction pattern, an energy dispersive x-ray spectrum, and a mass spectrum. The test data set comprises one or more of the following a Raman spectrum characteristic of the unknown material, a mid-infrared spectrum characteristic of the unknown material, an x-ray diffraction pattern characteristic of the unknown material, an energy dispersive x-ray spectrum characteristic of the unknown material, and a mass spectrum characteristic of the unknown material.

In another embodiment, each sublibrary is searched using a text query of the unknown material that compares the text query to a text description of the known material.

In yet another embodiment, the plurality of sublibraries are searched using a similarity metric comprising one or more of the following: an Euclidean distance metric, a spectral angle mapper metric, a spectral information divergence metric, and a Mahalanobis distance metric.

In still another embodiment, an image sublibrary is provided where the library contains a plurality of reference images generated by an image generating instrument associated with the image sublibrary. A test image characterizing an unknown material is obtained, wherein the test image data set is generated by the image generating instrument. The test image is compared to the plurality of reference images.

In a further embodiment, the present disclosure relates to a computer-implemented method of instrument weight factor determination. The method comprises the steps of: (a) identifying a plurality of spectroscopic instruments; (b) for each spectroscopic instrument, obtaining an instrument-specific first plurality of spectra and an instrument-specific second plurality of spectra from a plurality of samples using the spectroscopic instrument; and (c) selecting a set of instrument-specific weight values from a plurality of weight values, wherein the set includes an instrument-specific weight value for each of the plurality of spectroscopic instruments. The step (d) in the method comprises performing the following for the selected set of instrument-specific weight values: for each spectroscopic instrument, assigning a respective instrument-specific weight value from the selected set of weight values to each instrument-specific spectrum in the first and the second plurality of spectra, thereby generating an instrument-specific first plurality of weighted spectra and an instrument-specific second plurality of weighted spectra. The method further includes the steps of: (e) for the selected set of instrument-specific weight values, determining a corresponding indicator probability value from the first and the second plurality of weighted spectra; (f) repeating steps (c), (d), and (e) until a predetermined number of different sets of instrument-specific weight values are selected, thereby obtaining a plurality of indicator probability values; (g) selecting a target set of instrument-specific weight values as that set of instrument-specific weight values which corresponds to a highest indicator probability value in the plurality of indicator probability values; and (h) for each spectroscopic instrument, applying an instrument-specific weight value from the target set to one or more spectra obtained using the spectroscopic instrument.

In one embodiment, the step (c) in the foregoing method comprises: selecting a corresponding weight value from the plurality of weight values for each spectroscopic instrument in such a manner that the total of all weight values in the set of instrument-specific weight values equals to "1".

In an alternative embodiment, the present disclosure further relates to classification of samples and class-specific determination of instrument weight factors using a methodology similar to that described above.

In yet another embodiment, the present disclosure relates to a system that comprises computer executable program code. The program code, when executed by a processor, causes the processor to automatically perform the instrument weight factor determinations using the method steps outlined above. Thus, the weight factor determination process may be substantially automated with a suitably programmed processor.

In one embodiment, the present disclosure relates to a methodology that may be substantially automated and that is configurable to determine weights to be accorded to spectroscopic data from different spectroscopic data generating instruments for improved identification of unknown materials. Library spectra from known materials are divided into training and validation sets. Initial, instrument-specific weighting factors are determined using a weight grid or weight scale. The training and validation spectra are weighted with the weighting factors and indicator probabilities for various sets of "coarse" weighting factors are determined through an iterative process. The finally-selected set of coarse weighting factors is further "fine tuned" using a weight grid with finer values of weights. The instrument-specific finer weight values may be applied to test data sets (or spectra) of an unknown material as well as to the library spectra from corresponding spectroscopic instruments. Instrument-specific weights for each class of samples may also be computed for additional customization and accuracy.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DESCRIPTION OF THE EMBODIMENTS

Reference will now be made in detail to the embodiments of the present disclosure, examples of which are illustrated in the accompanying drawings. Wherever possible, the same reference numbers will be used throughout the drawings to refer to the same or like parts.

Figure 1:
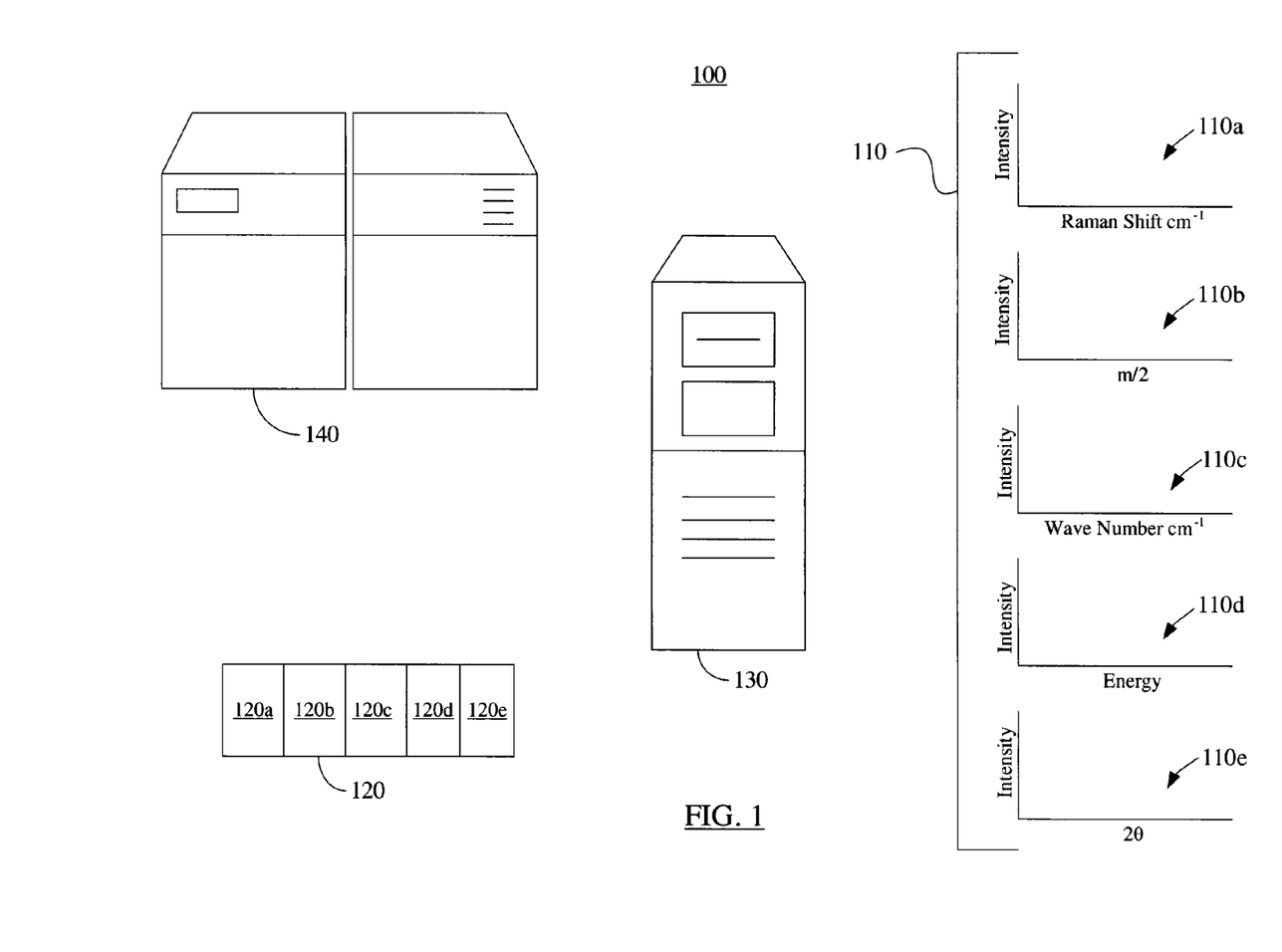
FIG. 1 illustrates an exemplary system of the present disclosure.

FIG. 1 illustrates an exemplary system 100 which may be used to carry out the methods of the present disclosure. System 100 may include a plurality of test data sets 110, a library 120, at least one processor 130, and a plurality of spectroscopic data generating instruments 140. The plurality of test data sets 110 may include data that are characteristics of an unknown material. The composition of the unknown material may include a single chemical composition or a mixture of chemical compositions.

The plurality of test data sets 110 may include data that characterizes an unknown material. The plurality of test data sets 110 may be obtained from a variety of instruments 140 that produce data representative of the chemical and physical properties of the unknown material. The plurality of test data sets may include spectroscopic data, text descriptions, chemical and physical property data, and chromatographic data. In one embodiment, the test data set includes a spectrum or a pattern that characterizes the chemical composition, molecular composition, physical properties and/or elemental composition of an unknown material. In another embodiment, the plurality of test data sets includes one or more of a Raman spectrum 110a, a mid-infrared spectrum 110b, an x-ray diffraction pattern 100c, an energy dispersive x-ray spectrum 110d, and a mass spectrum 110e that are characteristic of the unknown material. In yet another embodiment, the plurality of test data sets may also include image data set of the unknown material. In a still another embodiment, the test data set may include a physical property test data set selected from the group consisting of boiling point, melting point, density, freezing point, solubility, refractive index, specific gravity or molecular weight of the unknown material. In another embodiment, the test data set includes a textual description of the unknown material.

The plurality of spectroscopic data generating instruments 140 may include any analytical instrument which generates a spectrum, an image, a chromatogram, a physical measurement and a pattern characteristic of the physical properties, the chemical composition, or structural composition of a material. In one embodiment, the plurality of spectroscopic data generating instruments 140 includes a Raman spectrometer, a mid-infrared spectrometer, an x-ray diffractometer, an energy dispersive x-ray analyzer and a mass spectrometer. In another embodiment, the plurality of spectroscopic data generating instruments 140 further includes a microscope or image generating instrument. In yet another embodiment, the plurality of spectroscopic generating instruments 140 includes a chromatographic analyzer.

Library 120 may include a plurality of sublibraries 120a, 120b, 120c, 120d and 120e. Each sublibrary may be associated with a different spectroscopic data generating instrument 140. In one embodiment, the sublibraries include a Raman sublibrary, a mid-infrared sublibrary, an x-ray diffraction sublibrary, an energy dispersive sublibrary and a mass spectrum sublibrary. For this embodiment, the associated spectroscopic data generating instruments 140 include a Raman spectrometer, a mid-infrared spectrometer, an x-ray diffractometer, an energy dispersive x-ray analyzer, and a mass spectrometer. In another embodiment, the sublibraries further include an image sublibrary associated with a microscope. In yet another embodiment, the sublibraries further include a textual description sublibrary. In still yet another embodiment, the sublibraries further include a physical property sublibrary.

Each sublibrary 120a-120e may contain a plurality of reference data sets. The plurality of reference data sets may include data representative of the chemical and physical properties of a plurality of known materials. The plurality of reference data sets may include spectroscopic data, text descriptions, chemical and physical property data, and chromatographic data. In one embodiment, a reference data set includes a spectrum and a pattern that characterizes the chemical composition, the molecular composition and/or elemental composition of a known material. In another embodiment, the reference data set includes a Raman spectrum, a mid-infrared spectrum, an x-ray diffraction pattern, an energy dispersive x-ray spectrum, and a mass spectrum of known materials. In yet another embodiment, the reference data set further includes a physical property test data set of known materials selected from the group consisting of boiling point, melting point, density, freezing point, solubility, refractive index, specific gravity or molecular weight. In still another embodiment, the reference data set further includes an image displaying the shape, size and morphology of known materials. In another embodiment, the reference data set includes feature data having information such as particle size, color and morphology of the known material.

System 100 further includes at least one processor 130 in communication with the library 120 and its sublibraries 120a-120e. The processor 130 may be a programmable processor and may be configured to execute a set of instructions (or program code) to identify the composition of an unknown material. The processor 130 may be configured to "recognize" one or more of the spectroscopic data generating instruments 140 so as to automatically "communicate" with the specific instrument and also to obtain corresponding spectroscopic data therefrom.

In one embodiment, system 100 includes a library 120 having the following sublibraries: a Raman sublibrary associated with a Raman spectrometer; an infrared sublibrary associated with an infrared spectrometer; an x-ray diffraction sublibrary associated with an x-ray diffractometer; an energy dispersive x-ray sublibrary associated with an energy dispersive x-ray spectrometer; and a mass spectrum sublibrary associated with a mass spectrometer. The Raman sublibrary contains a plurality of Raman spectra characteristic of a plurality of known materials. The infrared sublibrary contains a plurality of infrared spectra characteristic of a plurality of known materials. The x-ray diffraction sublibrary contains a plurality of x-ray diffraction patterns characteristic of a plurality of known materials. The energy dispersive sublibrary contains a plurality of energy dispersive spectra characteristic of a plurality of known materials. The mass spectrum sublibrary contains a plurality of mass spectra characteristic of a plurality of known materials. The test data sets may include two or more of the following: a Raman spectrum of the unknown material, an infrared spectrum of the unknown material, an x-ray diffraction pattern of the unknown material, an energy dispersive spectrum of the unknown material, and a mass spectrum of the unknown material.

Figure 2A:
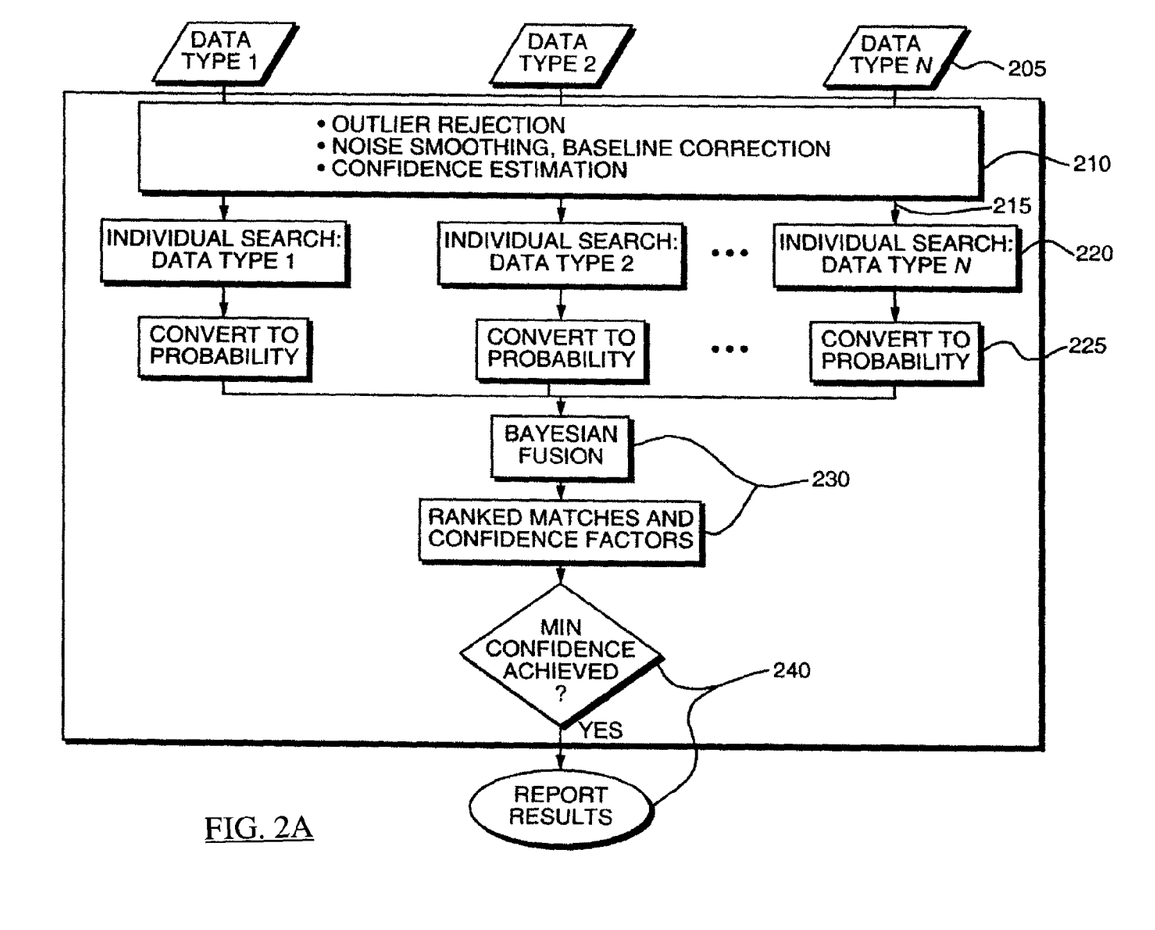
FIG. 2A illustrates an exemplary method of the present disclosure.

With reference to FIG. 2A, an exemplary method of the present disclosure is illustrated to determine the identification of an unknown material. In step 205, a plurality of test data sets characteristic of an unknown material are obtained from at least one of the different spectroscopic data generating instruments. In one embodiment, the plurality of test data sets 110 is obtained from one or more of the different spectroscopic data generating instruments 140. When a single spectroscopic data generating instrument is used to generate the test data sets, at least two or more test data sets may be required. In yet another embodiment, the plurality of test data sets 110 is obtained from at least two different spectroscopic data generating instruments.

In step 210, the test data sets are corrected to remove signals and information that are not due to the chemical composition of the unknown material. Algorithms known to those skilled in the art may be applied to the data sets to remove electronic noise and to correct the baseline of the test data set. The data sets may also be corrected to reject outlier data sets. In one embodiment, the processor 130 detects test data sets having signals and information that are not due to the chemical composition of the unknown material. These signals and information are then removed from the test data sets. In another embodiment, the user is issued a warning when the processor 130 detects test data set having signals and information that are not due to the chemical composition of the unknown material.

With further reference to FIG. 2A, each sublibrary is searched, in step 220. The searched sublibraries are those that are associated with the spectroscopic data generating instrument used to generate the test data sets. For example, when the plurality of test data sets includes a Raman spectrum of the unknown material and an infrared spectrum of the unknown material, the system searches the Raman sublibrary and the infrared sublibrary. In one embodiment, the sublibrary search is performed using a similarity metric that compares the test data set to each of the reference data sets in each of the searched sublibraries. In one embodiment, any similarity metric that produces a likelihood score may be used to perform the search. In another embodiment, the similarity metric includes one or more of an Euclidean distance metric, a spectral angle mapper metric, a spectral information divergence metric, and a Mahalanobis distance metric. The search results produce a corresponding set of scores for each searched sublibrary. The set of scores may contain a plurality of scores, one score for each reference data set in the searched sublibrary. Each score in the set of scores indicates a likelihood of a match between the test data set and each of reference data set in the searched sublibrary.

In step 225, the set of scores, produced in step 220, are converted to a set of relative probability values. The set of relative probability values may contain a plurality of relative probability values, one relative probability value for each reference data set.

Referring still to FIG. 2A, all relative probability values for each searched sublibrary are fused, in step 230, using the Bayes' probability rule. The fusion may produce a set of final probability values. The set of final probability values may contain a plurality of final probability values, one for each known material in the library. In one embodiment, the set of final probability values may be used to determine whether the unknown material is represented by a known material in the library.

In step 240, the identity of the unknown material is reported. To determine the identity of the unknown, in one embodiment, the highest final probability value from the set of final probability values is selected. This highest final probability value is then compared to a minimum confidence value. If the highest final probability value is greater than or equal to the minimum confidence value, the known material associated with the highest final probability value is reported. In one embodiment, the minimum confidence value may range from 0.70 to 0.95. In another embodiment, the minimum confidence value ranges from 0.8 to 0.95. In yet another embodiment, the minimum confidence value ranges from 0.90 to 0.95.

As described above, the library 120 may contain several different types of sublibraries, each of which may be associated with an analytical technique, i.e., the spectroscopic data generating instrument 140. Therefore, each analytical technique may provide an independent contribution to identifying the unknown material. Additionally, each analytical technique may have a different level of specificity for matching a test data set for an unknown material with a reference data set for a known material. For example, a Raman spectrum generally has a higher discriminatory power than a fluorescence spectrum and is thus considered more specific for the identification of an unknown material. The greater discriminatory power of Raman spectroscopy manifests itself as a higher likelihood for matching any given spectrum using Raman spectroscopy than using fluorescence spectroscopy. The method illustrated in FIG. 2A accounts for this variability in discriminatory power in the set of scores for each spectroscopic data generating instrument. In one embodiment, the set of scores act as implicit weighting factors that bias the scores according to the discriminatory power of the instrument. While the set of scores act as implicit weighting factors, the method of the present disclosure also provides for using explicit weighting factors. In one embodiment the explicit weighting factor for each spectroscopic data generating instrument is the same. In another embodiment the set of weighting factors includes the set $\{W\}=\{W_{Raman}, W_{x-ray}, W_{MassSpec}, W_{IR},$ and $W_{ED}\}$, which contains individual, instrument-specific weighting factors.

In yet another embodiment, as noted before, each spectroscopic data generating instrument may have a different associated weighting factor. Estimates of these associated weighting factors may be determined through automated simulations or as described in detail below. In particular, with at least two data records for each spectroscopic data generating instrument 140 (e.g., two Raman spectra per material), the library 120 may be split into training and validation sets as part of the instrument-specific weight factor determination according to one embodiment of the present disclosure and as depicted in the exemplary flowchart of FIG. 2B. In one embodiment, the training set is then used as the reference data set and the validation set (also referred to hereinbelow as a "prediction set") is used as the test data set and searched against the training set. Without instrument-specific weighting factors (i.e., when $\{W\}=\{1, 1, \ldots 1\}$), a certain percentage of the validation set will be correctly identified, and some percentage will be incorrectly identified. By explicitly or randomly varying the weighting factors and recording each set of correct and incorrect identification rates, the optimal operating set of weighting factors, for each spectroscopic data generating instrument, may be estimated by choosing those weighting factors that result in the best identification rates.

Figure 2B:
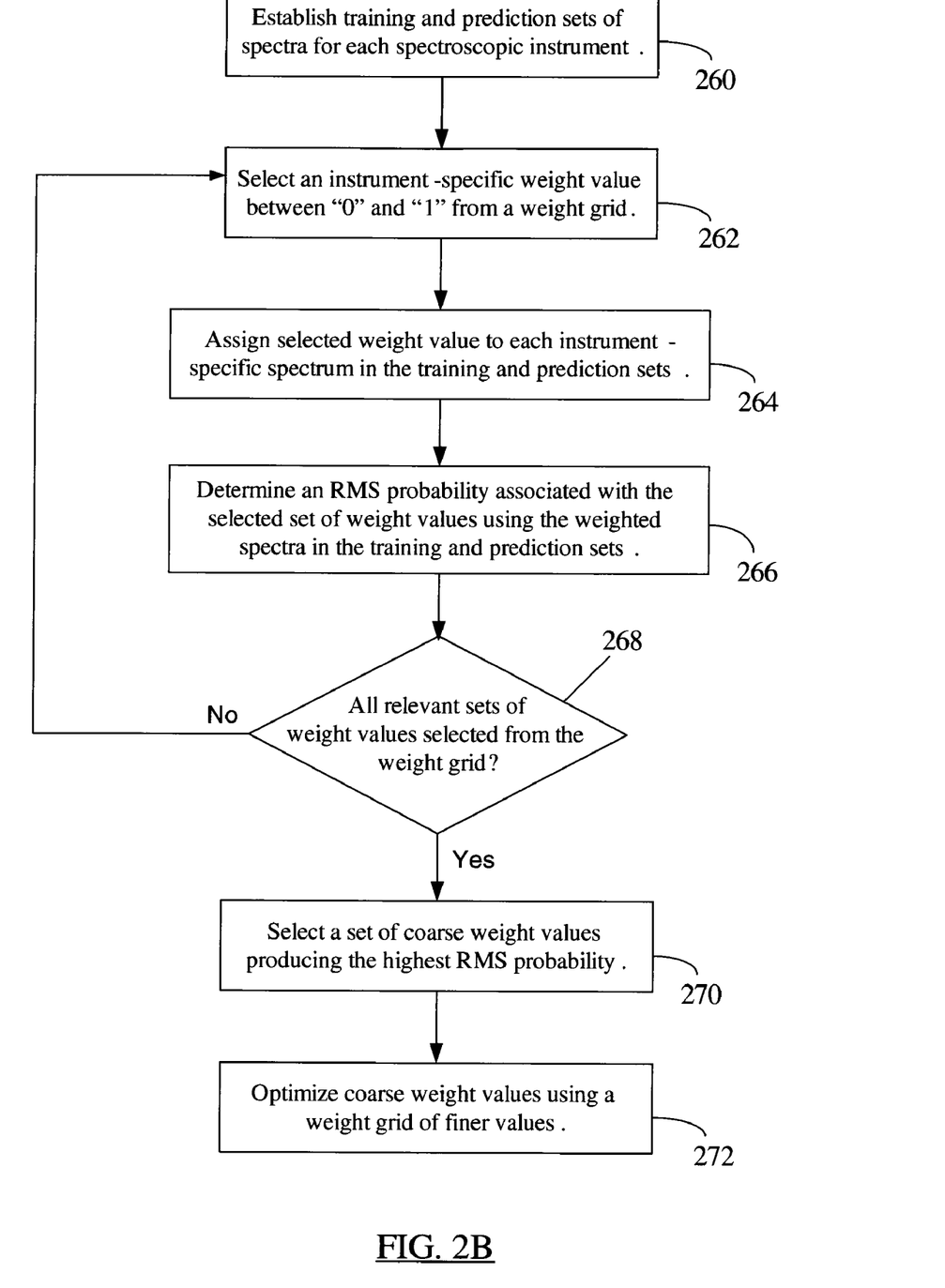
FIG. 2B depicts an exemplary flowchart for instrument-specific weight factor determination according to one embodiment of the present disclosure.

To determine weighting factors, in one embodiment, a training set may be established containing a predetermined number of library spectra from a plurality of spectroscopic data generating instruments as indicated at block 260 in FIG. 2B. For example, in case of two spectroscopic instruments—one Raman and one fluorescence—the training set may include Raman and fluorescence spectra from a hundred (100) library samples in an exemplary embodiment. Thus, a total of 200 spectra-two (Raman and fluorescence) spectra per library sample—may be contained in the training set. Similarly, a prediction (or validation) set may be established with spectra corresponding in number to the spectra in the training set as also indicated at block 260 in FIG. 2B. In one embodiment, the spectra for the validation set may be obtained from a different location in each sample than the corresponding sample locations from which respective training spectra are obtained. For example, if the training spectra (e.g., Raman and fluorescence) for a sample are obtained from a first location on the sample, then the prediction spectra (e.g., Raman and fluorescence) for that sample may be obtained from a second, different location on the same sample. This procedure may be carried out for all the samples to thereby obtain another 200 prediction spectra—two spectra (Raman and fluorescence) per sample in the example discussed herein. Thus, in the exemplary embodiment here, a total of 400 spectra may be collected.

It is noted here that although the term "spectrum" and its plural "spectra" are used herein with reference to discussion of training and prediction sets, these terms may be construed as referring to a "spectral data set" or "spectroscopic data set" in an electronic format (e.g., a digital format) as opposed to a pictorial or analog representation of a spectrum. Thus, for example, a "spectrum" or "spectral data set" may be collected from a sample location using a spectroscopic data generating instrument 140 (FIG. 1) and such "spectrum" or "spectral data set" may be stored or represented as an electronic data set in the corresponding training or prediction sets. Although this "spectrum" may be later viewed as an analog waveform on a display screen, the various data processing discussed hereinbelow with reference to FIG. 2B may be conveniently carried out using the electronic data format of that "spectrum."

In one embodiment, as part of a coarse grid-search optimization methodology to adjust or determine the "optimal" weighting factors that may be applied to spectra obtained from various spectroscopic instruments 140, a predetermined number of weights may be initially selected to represent a "weight grid" or "weight scale." For example, in one embodiment, eleven (11) different weight values may be selected between the grid values of zero (0) and one (1) in the increment of 0.1 as indicated at block 262 in FIG. 2B. In one embodiment, these weight values may be: 0, 0.1, 0.2, 0.3, 0.4, 0.5, 0.6, 0.7, 0.8, 0.9, and 1. A group of "M" of these weight values may be initially selected to be assigned to each of the M spectroscopic data generating instruments. In one embodiment, the "M" weight values may be randomly selected (e.g., by the processor 130 upon being suitably programmed) instead of selection of a predetermined set of "M" values. In another embodiment, the weight values in each group of M values may add up to "1" as discussed below.

In case of two (M=2) spectroscopic instruments—Raman and fluorescence—as mentioned above, a weight value=0 may be initially assigned to each Raman spectrum in the training set (of 100 Raman spectra) and another weight value=1 may be assigned to each fluorescence spectrum in the training set library (block 264, FIG. 2B). As noted before, it is preferable that the combination of selected weight values adds up to "1." The same weight values ($W_{raman}=0$, $W_{fl}=1$)

may also be assigned to each corresponding spectrum in the prediction set as indicated at block 264 in FIG. 2B. Thereafter, for each weighted sample spectrum in the prediction set, a library search of the weighted training set sample spectra may be performed and a corresponding set of final probability values may be obtained as discussed hereinbefore with reference to steps 220, 225, and 230 in FIG. 2A with reference to a test data set. In other words, during the weighting determination phase, each weighted spectrum in the prediction set may be treated as a "test data set" with respect to the weighted spectra (or "reference data sets") in the training set when iterations of the foregoing method of FIG. 2A are being performed. At the conclusion of the process depicted at steps 220, 225, and 230 in FIG. 2A, one may obtain 100 final probability values (each value corresponding to a specific sample in the prediction set) for a specific pair of instrument-specific weight values (here, $W_{raman}=0$, $W_{fl}=1$) in the exemplary embodiment under discussion here. As indicated at block 266 in FIG. 2B, the final probability values thus obtained may be used to calculate a weight pair-specific indicator probability value. In one embodiment, the indicator probability value is a root mean square (RMS) probability, which may be computed using the following equation:

RMS Probability $$(W_{raman}, W_{fl}) = \sqrt{\frac{\sum_{i=1}^{N}(P_i)^2}{N}},$$

where "$P_i$" is the $i^{th}$ final probability value, and "N" represents the total number of final probability values (N=100 in the example here).

It is seen from the above that, in the embodiment under discussion here, the RMS probability value is associated with the selected group of "M" weights (here, a pair of weights: $W_{raman}=0$, $W_{fl}=1$, where M=2). Thereafter, a different group of weights (where all selected weights add up to "1") may be selected and the foregoing steps at blocks 262, 264, and 266 may be repeated to determine another RMS probability value for the selected group of weights as indicated by the decision block 268 in FIG. 2B. For example, various different weight pairs in the above example of Raman and fluorescence instruments may include such weight value pairs as {($W_{raman}=0.1$, $W_{fl}=0.9$); ($W_{raman}=0.2$, $W_{fl}=0.8$); . . . ($W_{raman}=0.5$, $W_{fl}=0.5$); . . . ; ($W_{raman}=1$, $W_{fl}=0$)}. These pairs may be selected from the following grid of eleven (11) weight values (wherein each pair of weight values adds up to "1" as mentioned earlier):

| $W_{raman}$ | 0.0 | 0.1 | 0.2 | 0.3 | 0.4 | 0.5 | 0.6 | 0.7 | 0.8 | 0.9 | 1.0 |
|---|---|---|---|---|---|---|---|---|---|---|---|
| $W_{fl}$ | 1.0 | 0.9 | 0.8 | 0.7 | 0.6 | 0.5 | 0.4 | 0.3 | 0.2 | 0.1 | 0.0 |

Thus, in case W=11 (eleven different weight pair values to choose from), a total of 11 RMS probability values may be computed—one RMS probability value for each weight pair (i.e., for each set of instrument-specific weights). The pair of weight values producing the highest RMS probability value may be then selected as coarse weighting factors for the corresponding spectroscopic instruments as indicated at block 270 in FIG. 2B. For example, in case of the above exemplary Raman and fluorescence spectroscopic instruments and corresponding sample spectra in training and prediction sets, the above-described process may indicate that the "optimal" coarse weight values are: $W_{raman}=0.7$ and $W_{fl}=0.3$. A different set of weight values may be obtained with a different set of training and prediction spectra.

In one embodiment, as indicated at block 272 in FIG. 2B, a further optimization of the coarse grid/weight values may be carried out using a fine-scale optimization on approximate weights determined by the coarse grid-search methodology discussed above. During fine-scaling, a narrow range of weight values around the finalized coarse values may be selected and divided into a predetermined number of "finer" values. For example, in case of the exemplary coarse values of $W_{raman}=0.7$ and $W_{fl}=0.3$ mentioned above, the narrow range of values for fine-scale optimization may be: $W_{raman}$ from 0.6 to 0.8, and respective $W_{fl}$ from 0.4 to 0.2. Again, as noted before, it may be preferable to have each pair of weight values add up to "1." This new range of values may then be divided into another set of eleven (11) finer values as given below:

| $W_{raman}$ | 0.6 | 0.62 | 0.64 | 0.66 | 0.68 | 0.70 | 0.72 | 0.74 | 0.76 | 0.78 | 0.80 |
|---|---|---|---|---|---|---|---|---|---|---|---|
| $W_{fl}$ | 0.4 | 0.38 | 0.36 | 0.34 | 0.32 | 0.30 | 0.28 | 0.26 | 0.24 | 0.22 | 0.20 |

The earlier-described iterative method (blocks 262, 264, 266, 2768 and 270 in FIG. 2B) to calculate a final pair of coarse weighting factors may be now repeated for the above set of finer values. Thus, using different pairs of weight values (from a total of 11 pairs mentioned above) from the above grid of finer values, a corresponding RMS probability value can be obtained (as discussed before with reference to the process in FIG. 2B) for each pair of finer values. Finally, the pair of finer values producing the highest RMS probability value may be selected as "optimal" weighting factors for the given pair of spectroscopic instruments. For example, the above iterative calculations (using the process flow in FIG. 2B) may indicate that $W_{raman}=0.72$ and $W_{fl}=0.28$ provide the highest RMS probability value. In that case, these finer weight values ($W_{raman}=0.72$ and $W_{fl}=0.28$) may be then selected as weighting factors for corresponding spectroscopic instruments and may be applied to future test data sets or spectra collected from those instruments in the manner discussed earlier above. If further accuracy is desired, another range of values around the finally selected finer set of values may be selected and divided into suitable increments. The above iterative process in FIG. 2B can then be repeated to obtain yet finer weighting factors for the spectroscopic data generating instruments at issue. For example, in the present example, $W_{raman}$ may be selected from 0.7 to 0.74 and corresponding $W_{fl}$ may be selected from 0.30 to 0.26. This range may be then further divided to obtain still finer values for the weighting factors using the RMS probability criterion as discussed above.

It is observed here that the above described grid-search based weighting factor determination methodology (FIG. 2B) is not restricted to weight determinations (coarse or fine) for just two spectroscopic instruments (as is the case in the foregoing discussion of an exemplary embodiment). Thus, the methodology may be implemented in case of any number of spectroscopic data generating instruments 140 (e.g., $M \geq 3$). For example, in case of three different spectroscopic instruments (M=3) (e.g., a Raman spectrometer, a fluorescence spectrometer, and an MIR (mid-infrared) spectrometer), similar coarse weights may be initially assigned in such a manner that all the weights add up to "1." Some exemplary initial sets of coarse weights (e.g., weights to be used at block 262 during the first iteration of the process in FIG. 2B) may be ($W_{raman}$=0, $W_{fl}$=0.5, $W_{MIR}$=0.5) or ($W_{raman}$=0.5, $W_{fl}$=0, $W_{MIR}$=0.5). As noted before, the initial weight values may be predetermined or may be randomly selected (e.g., by the processor 130). Similarly, in case of an exemplary set of four different spectroscopic instruments (M=4) (e.g., a Raman spectrometer, a fluorescence spectrometer, an MIR spectrometer, and a mass spectrometer), an initial set of coarse weight values may be ($W_{raman}$=0.25, $W_{fl}$=0.25, $W_{MIR}$=0.25, $W_{mass}$=0.25). Similar initial weight values may be selected (in a predetermined or random manner) in case of other sets of spectroscopic instruments. In one embodiment, as noted before, different selected weight values (coarse or fine) may all add up to "1."

The above-described weight determination process in FIG. 2B may be repeated every time the reference spectral library of the training set is updated, so as to incorporate the new sample spectra into the weight determinations. A corresponding new set of prediction spectra may also be needed for the newly-added samples to carry out the weight determinations as discussed hereinbefore. In one embodiment, prior to performing a library search (e.g., using the approach illustrated in FIG. 2A), the finally-determined set of instrument-specific weights may be used to "weight" or "bias" the library spectra as well as test data sets (or spectra) of unknown samples collected using corresponding spectroscopic data generating instruments. Thus, instrument-specific weight may be applied to spectra collected using the corresponding instrument.

In one embodiment, different mathematical analysis methods may be used to determine weighting factors using only the training set of library spectra (instead of using the training set as well as a separate prediction set as discussed hereinbefore). In another embodiment, in the absence of a prediction set, the training set itself may be partitioned to carry out weight determinations in a manner similar to that discussed hereinbefore with reference to FIG. 2B.

Aside from the grid-search based weighting factor determination discussed above, alternative methods such as the simplex method, the simulated annealing method, various genetic algorithms, and the gradient method may also be used to determine weighting factors.

In a further embodiment, the reference library spectra in the training set and corresponding spectra in the prediction set may be divided into different abstract classes of spectra as desired by the user. Alternatively, the division of spectra into abstract classes may be carried out automatically in software using cluster analysis techniques. For example, the processor 130 may be configured by the software to perform cluster analysis techniques for such division of spectra into abstract classes. In one embodiment, one class of spectra may contain spectra from explosive materials, other class of spectra may contain spectra from biothreat agents, etc. It is observed here that some sample spectra may be present in more than one class. In one embodiment, separate, class-specific weighting factors (for spectroscopic instruments) may be determined for each class using the spectra associated with that class (in the training and prediction sets) and the grid-search based weighting factor determination methodology discussed hereinbefore with reference to FIG. 2B. In such class-specific weighting factor determination, the same set of spectroscopic instruments may have different sets of weighting factors associated with them depending on the respective class. For example, in case of two spectroscopic instruments (e.g., a Raman spectrometer, and a fluorescence spectrometer) and the class of explosive materials, the exemplary fine weight values may be: $W_{raman}$=0.763, and $W_{fl}$=0.237. However, the same spectroscopic instruments may have different weight values in case of the class of biothreat agents. In such a case, for example, the weight values may be: $W_{raman}$=0.659 and $W_{fl}$=0.341. The methodology discussed hereinbefore with reference to FIG. 2B may be easily adapted to determine such class-specific weighting factors and, hence, additional discussion of class-specific weighting factor determination is not provided herein for the sake of brevity.

In one embodiment, during operation, when an unknown spectrum or test data set is presented to the spectral library 120 for a search, the processor 130 may be configured to automatically determine to which class the unknown spectrum belongs. The processor 130 may then use the instrument-specific weights associated with that class for the search of the library 120 with that input (unknown) spectrum. Alternatively, in one embodiment, a user may be allowed to indicate the class to which the unknown spectrum belongs and the processor 130 may then use the weights specific to that user-specified class for the spectral search. The class-specific weighting may allow additional customization of spectral searching methodologies discussed herein and may also provide further accuracy in identification of unknown materials.

Thus, the system 100 may include a computer-executable program code (not shown in FIG. 1) that, when executed by the processor 130, may cause the processor 130 to perform various different weight determination tasks (e.g., instrument-specific weight determinations using a grid-search methodology, or class-specific weight determinations for a given set of spectroscopic instruments, etc.) discussed hereinbefore. The process of weighting factor determination may be thus substantially automated with suitably programmed processor 130. The processor 130 may be configured to "recognize" various spectroscopic instruments 140 in the system 100 and may collect spectra (e.g., for the training and validation sets) from those instruments 140 to carry out weighting factor determination using, for example, the methodology discussed hereinbefore with reference to FIG. 2B. In one embodiment, a user may be allowed to identify the samples from which spectra may be collected or obtained for the training and validation sets. The processor 130 may then process spectra from those user-identified samples.

In one embodiment, the processor 130 may be configured to display (e.g., on a display screen such as a computer display or monitor (not shown)) or otherwise make available to a user the weighting factors (e.g., coarse and/or fine) determined according to various methodologies or approaches discussed hereinbefore.

The method of the present disclosure also provides for using a text query to limit the number of reference data sets of known compounds in the sublibrary searched in step 220 of FIG. 2A. In that case, the method illustrated in FIG. 2A would further include step 215, where each sublibrary is searched, using a text query. Each known material in the plurality of sublibraries may include a text description of a physical property or a distinguishing feature of the material. A text query, describing the unknown material may be submitted. The plurality of sublibraries may be searched by comparing the text query to a text description of each known material. A match of the text query to the text description or no match of the text query to the text description is produced. The plurality of sublibraries may be modified by removing the reference data sets that produced a no match answer. Therefore, the modified sublibraries have fewer reference data sets than the original sublibraries. For example, a text query for "white powders" eliminates the reference data sets from the sublibraries for any known compounds having a textual description of "black powders." The modified sublibraries are then searched as described for steps 220-240 in FIG. 2A.

In one embodiment, the method of the present disclosure also provides for using images to identify the unknown material. In one embodiment, an image test data set characterizing an unknown material is obtained from an image generating instrument. The test image, of the unknown, is compared to the plurality of reference images for the known materials in an image sublibrary to assist in the identification of the unknown material. In another embodiment, a set of test feature data is extracted from the image test data set using a feature extraction algorithm to generate test feature data. The selection of an extraction algorithm is well known to one of skill in the art of digital imaging. The test feature data may include information concerning particle size, color or morphology of the unknown material. The test feature data is searched (in the manner discussed hereinbefore with reference to FIG. 2A) against the reference feature data in the image sublibrary, producing a set of scores. The reference feature data may include information such as particle size, color and morphology of the material. The set of scores, from the image sublibrary, are used to calculate a set of probability values. The relative probability values, for the image sublibrary, are fused with the relative probability values for the other plurality of sublibraries as illustrated in FIG. 2A, step 230, thereby producing a set of final probability values. The known material represented in the library, having the highest final probability value is reported if the highest final probability value is greater than or equal to a minimum confidence value as in step 240 of FIG. 2A.

In one embodiment, the method of the present disclosure further provides for enabling a user to view one or more reference data sets of the known material identified as representing the unknown material despite the absence of one or more test data sets. For example, the user may input an infrared test data set and a Raman test data set to the system. The x-ray dispersive spectroscopy ("EDS") sublibrary contains an EDS reference data set for the plurality of known compounds even though the user did not input an EDS test data set. Using the steps illustrated in FIG. 2A, the system identifies a known material, characterized in the infrared and Raman sublibraries, as having the highest probability of matching the unknown material. The system then enables the user to view an EDS reference data set, from the EDS sublibrary, for the known material having the highest probability of matching the unknown material. In another embodiment, the system enables the user to view one or more EDS reference data sets for one or more known materials having a high probability of matching the unknown material.

In one embodiment, the method of the present disclosure also provides for identifying unknowns when one or more of the sublibraries are missing one or more reference data sets. When a sublibrary has fewer reference data sets than the number of known materials characterized within the main library, the system may treat this sublibrary as an incomplete sublibrary. In one embodiment, to obtain a score for the missing reference data set, the system may calculate a mean score based on the set of scores, from step 225 (FIG. 2A), for the incomplete library. The mean score is then used, in the set of scores, as the score for the missing reference data set.

In another embodiment, the method of the present disclosure also provides for identifying miscalibrated test data sets. When one or more of the test data sets fail to match any reference data set in the searched sublibrary, the system may treat the test data set as miscalibrated. The assumed miscalibrated test data sets may be processed via a grid optimization process where a range of zero and first order corrections are applied to the data to generate one or more corrected test data sets. The system then reanalyzes the corrected test data set using the steps illustrated in FIG. 2A. This same process may be applied during the development of the sublibraries to ensure that all the library spectra are properly calibrated. The sublibrary examination process identifies reference data sets that do not have any close matches, by applying the steps illustrated in FIG. 2A, to determine if changes in the calibration results in close matches.

Figure 3:
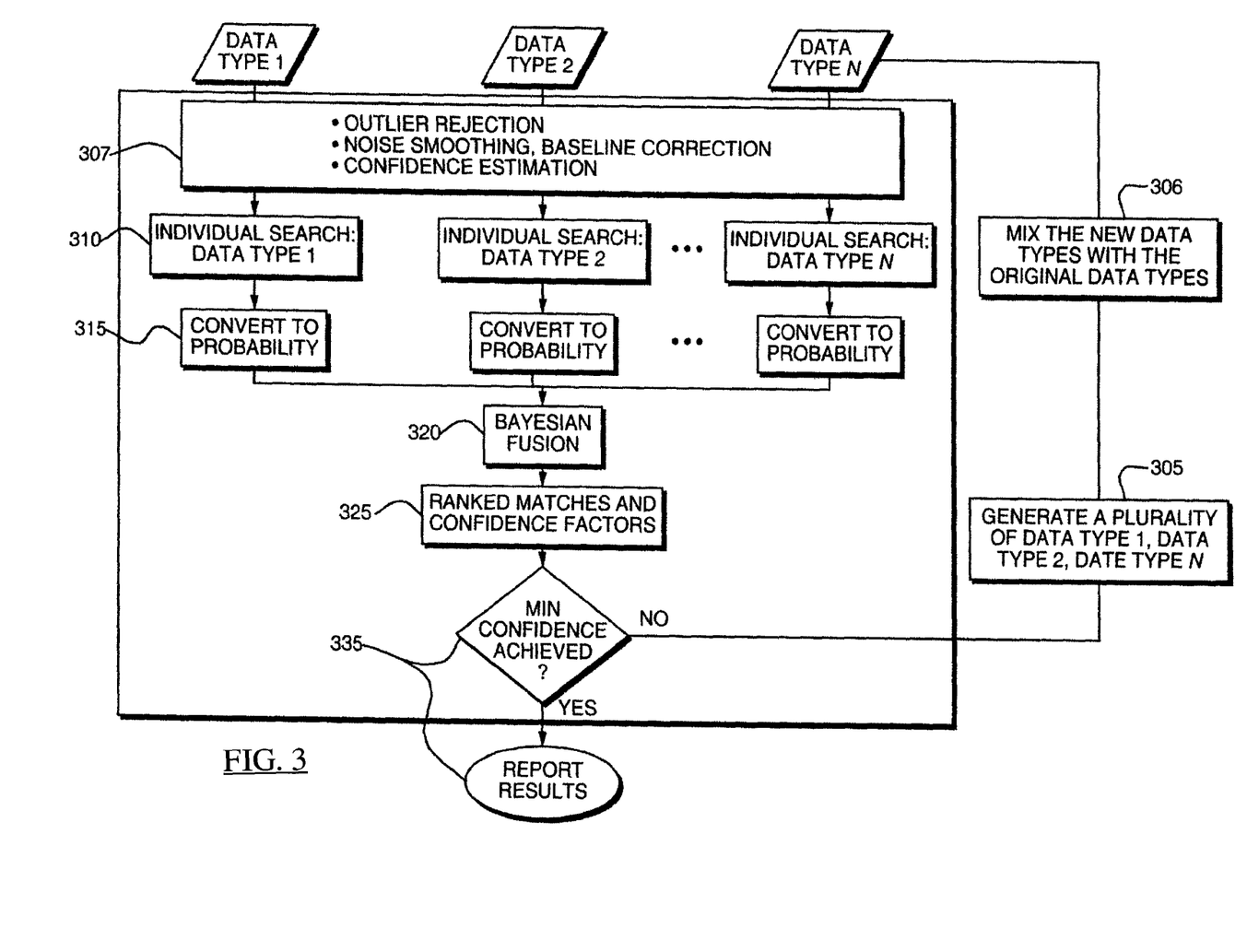
FIG. 3 illustrates another exemplary method of the present disclosure.

In a further embodiment, the method of the present disclosure also provides for the identification of the components of an unknown mixture. With reference to the embodiment in FIG. 2A, if the highest final probability value is less than the minimum confidence value, in step 240, the system of the present disclosure treats the unknown as a mixture. Referring to FIG. 3, a plurality of new test data sets, characteristic of the unknown material, are obtained in step 305. As discussed before, each new test data set is generated by one of the plurality of the different spectroscopic data generating instruments 140 (FIG. 1). In one embodiment, for each different spectroscopic data generating instrument 140, at least two new test data sets are obtained. In one embodiment, six to twelve new test data sets are obtained from a spectroscopic data generating instrument 140. The new test data sets may be obtained from several different locations of the unknown. The new test data sets at step 305 may be combined with the initial test data sets of step 205 in FIG. 2A, to generate combined test data sets as indicated at step 306 of FIG. 3. When the initial test data sets (step 205, FIG. 2A) are combined with the new test data sets (step 305, FIG. 3), the data sets must be of the same type in that they are generated by the same spectroscopic data generating instrument. For example, new test data sets generated by a Raman spectrometer may be combined with the initial test data sets also generated by a Raman spectrometer.

In step 307, the combined test data sets are corrected to remove signals and information that are not due to the chemical composition of the unknown material. In step 310, each sublibrary is searched for a match for each combined test data set. The searched sublibraries are associated with the spectroscopic data generating instrument used to generate the combined test data sets. The sublibrary search may be performed using a spectral unmixing metric that compares the plurality of combined test data sets to each of the reference data sets in each of the searched sublibraries. A spectral unmixing metric is disclosed in U.S. patent application Ser. No. 10/812,233 entitled "Method for Identifying Components of a Mixture via Spectral Analysis," filed Mar. 29, 2004 which is incorporated herein by reference in its entirety; however this application forms no part of the present invention. The sublibrary searching in the embodiment of FIG. 3 may produce a corresponding second set of scores for each searched sublibrary. Each second score and the second set of scores is the score and set of scores produced in the second pass of the searching method (as opposed to the first pass performed in conjunction with the performance of the process in FIG. 2A). Each second score in the second set of scores indicates a second likelihood of a match between a combined test data set and each of reference data sets in the searched sublibraries. The second set of scores contains a plurality of second scores, one second score for each reference data set in the searched sublibrary.

According to a spectral unmixing metric, the combined test data sets define an n-dimensional data space, where "n" is the number of points in the combined test data sets. Principal component analysis (PCA) techniques may be applied to the n-dimensional data space to reduce the dimensionality of the data space. This dimensionality reduction step may result in the selection of "m" eigenvectors as coordinate axes in the new data space. For each searched sublibrary, the reference data sets are compared to the reduced dimensionality data space generated from the combined test data sets using target factor testing techniques. Each sublibrary reference data set may be projected as a vector in the reduced m-dimensional data space. An angle between the sublibrary vector and the data space may result from the target factor testing. This may be performed by calculating the angles between the sublibrary reference data set and the projected sublibrary data. These angles may be used as the second scores which are converted to second probability values for each of the reference data sets and fed into the fusion algorithm in the second pass of the search method. However, the methodology discussed in this paragraph forms no part of the search methodologies presented in FIGS. 2A and 3.

Referring still to FIG. 3, second relative probability values are determined and the values are then fused in a manner similar to that discussed hereinbefore with reference to FIG. 2A. A second set of relative probability values are calculated for each searched sublibrary based on the corresponding second set of scores for each searched sublibrary (step 315). The second set of relative probability values is the set of probability values calculated in the second pass of the search method (i.e., the process in FIG. 3). The second relative probability values for each searched sublibrary are fused using the Bayes' probability rule to produce a second set of final probability values (step 320). The set of final probability values may be used in determining whether the unknown materials are represented by a set of known materials in the library.

From the set of second final probabilities values, a set of high second final probability values is selected. The set of high second final probability values is then compared to the minimum confidence value (step 325). If each high second final probability value is greater than or equal to the minimum confidence value (step 335), the set of known materials represented in the library having the high second final probability values is reported. In one embodiment, the minimum confidence value may range from 0.70 to 0.95. In another embodiment, the minimum confidence value may range from 0.8 to 0.95. In yet another embodiment, the minimum confidence value may range from 0.9 to 0.95.

Figure 4:
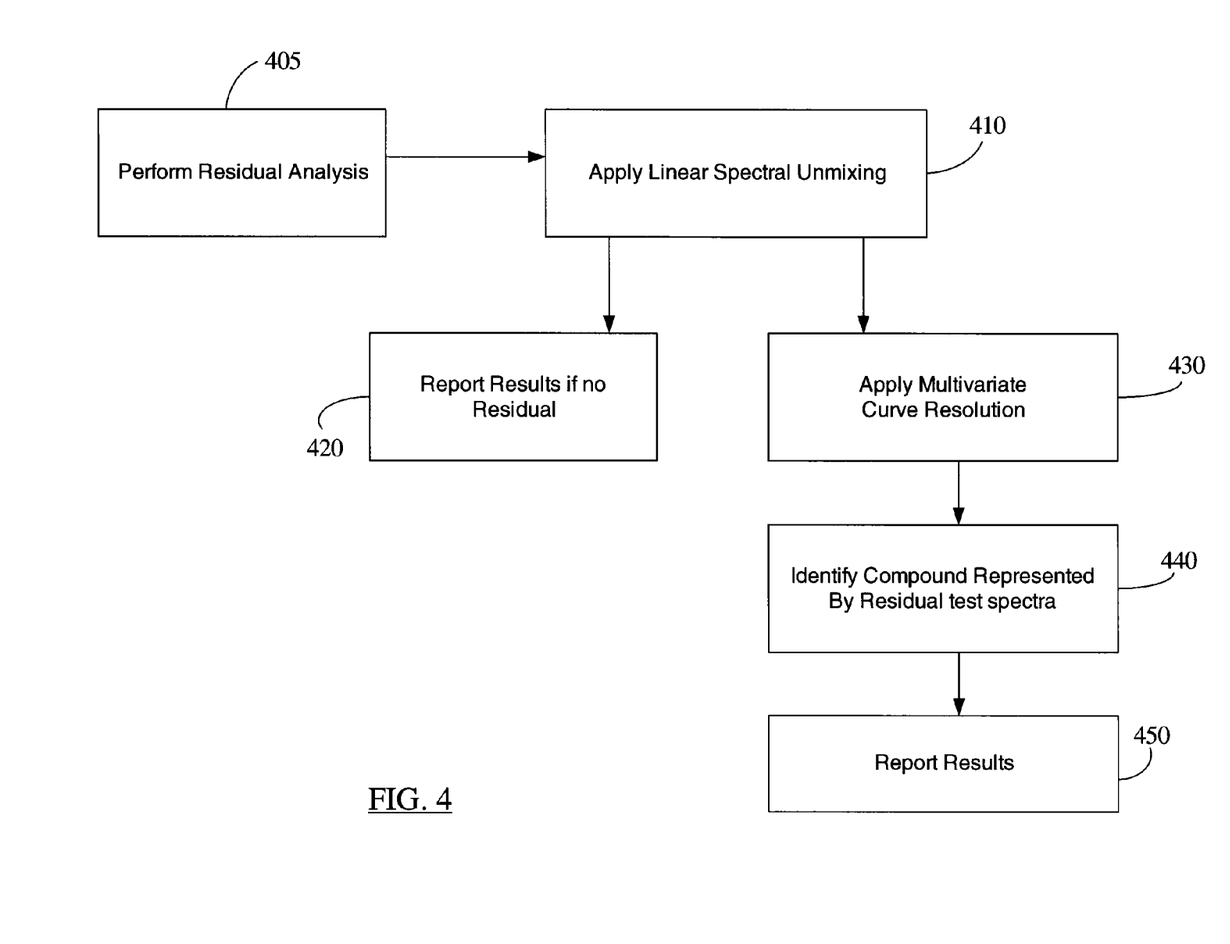
FIG. 4 illustrates a further exemplary method of the present disclosure.

Referring now to FIG. 4, a user may also perform a residual analysis (step 405). For each spectroscopic data generating instrument, residual data is defined by the following equation:

COMBINED TEST DATA SET=CONCENTRATION×REFERENCE DATA SET+RESIDUAL.

To calculate a residual data set, a linear spectral unmixing algorithm may be applied to the plurality of combined test data sets, to thereby produce a plurality of residual test data (step 410). Each searched sublibrary may have an associated residual test data. When a plurality of residual test data are not identified in step 410, a report is issued at step 420. In this step 420, the components of the unknown material are reported as those components determined in step 335 of FIG. 3. Residual data is determined when there is a significant percentage of variance explained by the residual as compared to the percentage explained by the reference data set defined in the above equation. When residual test data is determined in step 410, a multivariate curve resolution algorithm may be applied to the plurality of residual test data generating a plurality of residual data spectra in step 430. Each searched sublibrary may have a plurality of associated residual test spectra. In step 440, the identification of the compound corresponding to the plurality of residual test spectra is determined and the identification is then reported in step 450. In one embodiment, the plurality of residual test spectra are compared to the reference data set in the sublibrary, associated with the residual test spectra, to determine the compound associated with the residual test spectra. If residual test spectra do not match any reference data sets in the plurality of sublibraries, a report is issued stating an unidentified residual compound is present in the unknown material.

EXAMPLES

Example 1

This example relates to a network of n spectroscopic instruments, each instrument (e.g., instrument 140 in FIG. 1) providing test data sets to a central processing unit (e.g., the processor 130 in FIG. 1). Each instrument makes an observation vector $\{Z\}$ of parameter $\{x\}$. For instance, a dispersive Raman spectrum would be modeled with X=dispersive Raman and Z=the spectral data. Each instrument generates a test data set and the processing unit calculates (using a similarity metric) the likelihoods $\{p_i(H_a)\}$ of the test data set being of type $H_a$. Bayes' theorem gives:

$$p(H_a \mid \{Z\}) = \frac{p(\{Z\} \mid H_a) p(H_a)}{p(\{Z\})} \quad \text{(Equation 1)}$$

where:

$p(H_a|\{Z\})$: the posterior probability of the test data being of type $H_a$, given the observations $\{Z\}$;

$p(\{Z\}|H_a)$: the probability that observations $\{Z\}$ were taken, given that the test data is type $H_a$;

$p(H_a)$: the prior probability of type $H_a$ being correct; and $p(\{Z\})$: a normalization factor to ensure the posterior probabilities sum to 1.

Assuming that each spectroscopic instrument is independent of the other spectroscopic instruments, the following may be given:

$$p(\{Z\} \mid H_a) = \prod_{i=1}^{n} p_i(\{Z_i\} \mid H_a) \quad \text{(Equation 2)}$$

and from Bayes' rule $$p(\{Z\} \mid H_a) = \prod_{i=1}^{n} (p_i(\{Z_i\} \mid \{X\}) p_i(\{X\} \mid H_a)) \quad \text{(Equation 3)}$$

which gives $$p(H_a | \{Z\}) = \alpha \cdot p(H_a) \prod_{i=1}^{n} [(p_i(\{Z_i\} | \{X\}) p_i(\{X\} | H_a)] \quad \text{(Equation 4)}$$

Equation 4 is the central equation that uses Bayesian data fusion to combine observations from different spectroscopic instruments to give probabilities of the presumed identities.

To infer a presumed identity from the above Equation 4, a value of identity is assigned to the test data having the most probable (maximum a posteriori) result:

$$\hat{H}_a = \operatorname*{argmax}_a p(H_a | \{Z\}) \quad \text{(Equation 5)}$$

To use the above formulation (i.e., Equation 5), the test data is converted to probabilities. In particular, the spectroscopic instrument must give $p(\{Z\}|H_a)$, the probability that observations $\{Z\}$ were taken, given that the test data is type $H_a$. Each sublibrary is a set of reference data sets that match the test data set with certain probabilities. The probabilities of the unknown matching each of the reference data sets must sum to 1. The sublibrary is considered as a probability distribution.

The system (e.g., the processor 130 in FIG. 1) applies a few commonly used similarity metrics consistent with the requirements of this algorithm: Euclidean Distance, the Spectral Angle Mapper (SAM), the Spectral Information Divergence (SID), Mahalanobis distance metric and spectral unmixing. The SID has roots in probability theory and is thus a preferable choice for the use in the data fusion algorithm, although other choices will be technically compatible. Euclidean Distance ("ED") is used to give the distance between spectrum x and spectrum y:

$$ED(x, y) = \sqrt{\sum_{i=1}^{L} (x_i - y_i)^2} \quad \text{(Equation 6)}$$

Spectral Angle Mapper ("SAM") finds the angle between spectrum x and spectrum y:

$$SAM(x, y) = \cos^{-1}\left(\frac{\sum_{i=1}^{L} x_i y_i}{\sqrt{\sum_{i=1}^{L} x_i^2} \sqrt{\sum_{i=1}^{L} y_i^2}}\right) \quad \text{(Equation 7)}$$

When SAM is small, it is nearly the same as ED. Spectral Information Divergence ("SID") takes an information theory approach to similarity and transforms the x and y spectra into probability distributions p and q:

$$p = [p_1, p_2, \ldots, p_L]^T, \quad q = [q_1, q_2, \ldots, q_L]^T \quad \text{(Equation 8)}$$

$$p_i = \frac{x_i}{\sum_{i=1}^{L} x_i}, \quad q_i = \frac{y_i}{\sum_{i=1}^{L} y_i}$$

The discrepancy in the self-information of each band is defined as:

$$D_i(x_i \| y_i) = \log\left[\frac{p_i}{q_i}\right] \quad \text{(Equation 9)}$$

So the average discrepancies of x compared to y and y compared to x (which are different) are:

$$D(x \| y) = \sum_{i=1}^{L} p_i \log\left[\frac{p_i}{q_i}\right], \quad D(y \| x) = \sum_{i=1}^{L} q_i \log\left[\frac{q_i}{p_i}\right] \quad \text{(Equation 10)}$$

The SID is thus defined as:

$$SID(x,y) = D(x\|y) + D(y\|x) \quad \text{(Equation 11)}$$

A measure of the probabilities of matching a test data set with each entry in the sublibrary may be needed. Generalizing a similarity metric as m(x,y), the relative spectral discrimination probabilities is determined by comparing a test data set x against k library entries.

$$p_{x,Library}(k) = 1 - \frac{m(x, y_k)}{\sum_{i=1}^{L} m(x, y_i)} \quad \text{(Equation 12)}$$

In one embodiment, Equation 12 is used as $p(\{Z\}|H_a)$ for each sensor in the fusion formula.

Assuming a library consists of three reference data sets: $\{H\}=\{A, B, C\}$. Three spectroscopic instruments (each a different modality) are applied to this sample and the outputs of each spectroscopic instrument are compared to the appropriate sublibraries (e.g., dispersive Raman spectrum compared with library of dispersive Raman spectra, fluorescence spectrum compared with library of fluorescence spectra, etc.). If the individual search results, using SID, are:

$$SID(X_{Raman}, Library_{Raman}) = \{20,10,25\}$$

$$SID(X_{Fluor}, Library_{Fluor}) = \{40,35,50\}$$

$$SID(X_{IR}, Library_{IR}) = \{50,20,40\}$$

Applying Equation 12, the relative probabilities are:

$$p(Z_{\{Raman\}} | \{H\}) = \{0.63, 0.81, 0.55\}$$

$$p(Z_{\{Fluor\}} | \{H\}) = \{0.68, 0.72, 0.6\}$$

$$p(Z_{\{IR\}} | \{H\}) = \{0.55, 0.81, 0.63\}$$

It is assumed that each of the reference data sets is equally likely, with:

$$p(\{H\}) = \{p(H_A), p(H_B), p(H_C)\} = \{0.33, 0.33, 0.33\}$$

Applying Equation 4 results in:

$$p(\{H\}|\{Z\}) = \alpha \times \{0.33, 0.33, 0.33\} \times [\{0.63, 0.81, 0.55\} \cdot \{0.68, 0.72, 0.6\} \cdot \{0.55, 0.81, 0.63\}]$$

$$p(\{H\}|\{Z\}) = \alpha \times \{0.0779, 0.1591, 0.0687\}$$

Now normalizing with $\alpha = 1/(0.0779 + 0.1591 + 0.0687)$ results in:

$$p(\{H\}|\{Z\}) = \{0.25, 0.52, 0.22\}$$

The search identifies the unknown sample as reference data set B, with an associated probability of 52%.

Example 2

In this example, Raman and mid-infrared (MIR) sublibraries each having reference data set for 61 substances (or samples) were used. For each of the 61 substances, the Raman and mid-infrared sublibraries were searched using the Euclidean distance vector comparison. In other words, each substance is used sequentially as a target vector. The resulting set of scores for each sublibrary were converted to a set of probability values by first converting the score to a Z value and then looking up the probability from a Normal Distribution probability table. The process was repeated for each spectroscopic technique for each substance and the resulting probabilities were calculated. The set of final probability values was obtained by multiplying the two sets of probability values.

The results are displayed in Table 1 below. Based on the calculated probabilities, the top match (the score with the highest probability) was determined for each spectroscopic technique individually and for the combined probabilities. A value of "1" indicates that the target vector successfully found itself as the top match, while a value of "0" indicates that the target vector found some match other than itself as the top match. The Raman probabilities resulted in four incorrect results, the mid-infrared probabilities resulted in two incorrect results, and the combined probabilities resulted in no incorrect results.

The more significant result is the fact that the distance between the top match and the second match is significantly large for the combined approach as opposed to individual Raman or mid-infrared approaches for almost all of the 61 substances. In fact, 15 of the combined results have a difference that is four times greater distance than the distance for either MIR or Raman, individually. Only five of the 61 substances do not benefit from the fusion algorithm.

TABLE 1

| Index | Substance | Raman | MIR | Combined | Raman Distance | MIR Distance | Combined Distance |
|---|---|---|---|---|---|---|---|
| 1 | 2-Propanol | 1 | 1 | 1 | 0.0429 | 0.0073 | 0.0535 |
| 2 | Acetamidophenol | 1 | 1 | 1 | 0.0406 | 0.0151 | 0.2864 |
| 3 | Acetone | 1 | 1 | 1 | 0.0805 | 0.0130 | 0.2294 |
| 4 | Acetonitrile | 1 | 1 | 1 | 0.0889 | 0.0167 | 0.4087 |
| 5 | Acetylsalicylic Acid | 1 | 1 | 1 | 0.0152 | 0.0152 | 0.0301 |
| 6 | Ammonium Nitrate | 0 | 1 | 1 | 0.0000 | 0.0467 | 0.0683 |
| 7 | Benzalkonium Chloride | 1 | 1 | 1 | 0.0358 | 0.0511 | 0.1070 |
| 8 | Caffeine | 1 | 1 | 1 | 0.0567 | 0.0356 | 0.1852 |
| 9 | Calcium Carbonate | 1 | 1 | 1 | 0.0001 | 0.0046 | 0.0047 |
| 10 | Calcium chloride | 1 | 1 | 1 | 0.0187 | 0.0076 | 0.2716 |
| 11 | Calcium Hydroxide | 1 | 1 | 1 | 0.0009 | 0.0006 | 0.0015 |
| 12 | Calcium Oxide | 1 | 1 | 1 | 0.0016 | 0.0848 | 0.1172 |
| 13 | Calcium Sulfate | 0 | 1 | 1 | 0.0000 | 0.0078 | 0.2818 |
| 14 | Cane Sugar | 1 | 1 | 1 | 0.0133 | 0.0006 | 0.0137 |
| 15 | Charcoal | 1 | 1 | 1 | 0.0474 | 0.0408 | 0.1252 |
| 16 | Cocaine pure | 1 | 1 | 1 | 0.0791 | 0.0739 | 0.2261 |
| 17 | Creatine | 1 | 1 | 1 | 0.1102 | 0.0331 | 0.3751 |
| 18 | D-Fructose | 1 | 1 | 1 | 0.0708 | 0.0536 | 0.1336 |
| 19 | D-Amphetamine | 1 | 0 | 1 | 0.0400 | 0.0000 | 0.0400 |
| 20 | Dextromethorphan | 1 | 1 | 1 | 0.0269 | 0.1067 | 0.2940 |
| 21 | Dimethyl Sulfoxide | 1 | 1 | 1 | 0.0069 | 0.0466 | 0.1323 |
| 22 | D-Ribose | 1 | 1 | 1 | 0.0550 | 0.0390 | 0.1314 |
| 23 | D-Xylose | 1 | 1 | 1 | 0.0499 | 0.0296 | 0.1193 |
| 24 | Ephedrine | 1 | 1 | 1 | 0.0367 | 0.0567 | 0.2067 |
| 25 | Ethanol_processed | 1 | 1 | 1 | 0.0269 | 0.0276 | 0.1574 |
| 26 | Ethylene Glycol | 1 | 1 | 1 | 0.1020 | 0.0165 | 0.1692 |
| 27 | Ethylenediamine-tetraacetate | 1 | 1 | 1 | 0.0543 | 0.0312 | 0.2108 |
| 28 | Formula 409 | 1 | 1 | 1 | 0.0237 | 0.0063 | 0.0663 |
| 29 | Glycerol GR | 1 | 1 | 1 | 0.0209 | 0.0257 | 0.1226 |
| 30 | Heroin | 1 | 1 | 1 | 0.0444 | 0.0241 | 0.2367 |
| 31 | Ibuprofen | 1 | 1 | 1 | 0.0716 | 0.0452 | 0.2785 |
| 32 | Ketamine | 1 | 1 | 1 | 0.0753 | 0.0385 | 0.2954 |
| 33 | Lactose Monohydrate | 1 | 1 | 1 | 0.0021 | 0.0081 | 0.0098 |
| 34 | Lactose | 1 | 1 | 1 | 0.0021 | 0.0074 | 0.0092 |
| 35 | L-Amphetamine | 1 | 0 | 1 | 0.0217 | 0.0000 | 0.0217 |
| 36 | Lidocaine | 1 | 1 | 1 | 0.0379 | 0.0418 | 0.3417 |
| 37 | Mannitol | 1 | 1 | 1 | 0.0414 | 0.0361 | 0.0751 |
| 38 | Methanol | 1 | 1 | 1 | 0.0996 | 0.0280 | 0.1683 |
| 39 | Methcathinone-HCl | 1 | 1 | 1 | 0.0267 | 0.0147 | 0.0984 |
| 40 | Para-methoxymethyl-amphetamine | 1 | 1 | 1 | 0.0521 | 0.0106 | 0.0689 |
| 41 | Phenobarbital | 1 | 1 | 1 | 0.0318 | 0.0573 | 0.1807 |
| 42 | Polyethylene Glycol | 1 | 1 | 1 | 0.0197 | 0.0018 | 0.1700 |
| 43 | Potassium Nitrate | 0 | 1 | 1 | 0.0000 | 0.0029 | 0.0125 |
| 44 | Quinine | 1 | 1 | 1 | 0.0948 | 0.0563 | 0.2145 |
| 45 | Salicylic Acid | 1 | 1 | 1 | 0.0085 | 0.0327 | 0.2111 |
| 46 | Sildenfil | 1 | 1 | 1 | 0.1049 | 0.0277 | 0.1406 |
| 47 | Sodium Borate Decahydrate | 1 | 1 | 1 | 0.0054 | 0.0568 | 0.0618 |
| 48 | Sodium Carbonate | 1 | 1 | 1 | 0.0001 | 0.0772 | 0.0915 |
| 49 | Sodium Sulfate | 1 | 1 | 1 | 0.0354 | 0.0023 | 0.3190 |

TABLE 1-continued

| Index | Substance | Raman | MIR | Combined | Raman Distance | MIR Distance | Combined Distance |
|---|---|---|---|---|---|---|---|
| 50 | Sodium Sulfite | 1 | 1 | 1 | 0.0129 | 0.0001 | 0.3655 |
| 51 | Sorbitol | 1 | 1 | 1 | 0.0550 | 0.0449 | 0.1178 |
| 52 | Splenda Sugar Substitute | 1 | 1 | 1 | 0.0057 | 0.0039 | 0.0093 |
| 53 | Strychnine | 1 | 1 | 1 | 0.0710 | 0.0660 | 0.2669 |
| 54 | Styrofoam | 1 | 1 | 1 | 0.0057 | 0.0036 | 0.0453 |
| 55 | Sucrose | 1 | 1 | 1 | 0.0125 | 0.0005 | 0.0128 |
| 56 | Sulfanilamide | 1 | 1 | 1 | 0.0547 | 0.0791 | 0.1330 |
| 57 | Sweet N Low | 1 | 1 | 1 | 0.0072 | 0.0080 | 0.0145 |
| 58 | Talc | 0 | 1 | 1 | 0.0000 | 0.0001 | 0.5381 |
| 59 | Tannic Acid | 1 | 1 | 1 | 0.0347 | 0.0659 | 0.0982 |
| 60 | Tide detergent | 1 | 1 | 1 | 0.0757 | 0.0078 | 0.2586 |
| 61 | Urea | 1 | 1 | 1 | 0.0001 | 0.0843 | 0.1892 |

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the embodiments of the disclosure, it is noted that other variations and modification will be apparent to those skilled in the art, and may be made without departing from the spirit or scope of the disclosure.

What is claimed is:

1. A method comprising configuring a processor to perform the following steps: (a) identifying a plurality of spectroscopic instruments; (b) for each spectroscopic instrument, obtaining an instrument-specific first plurality of spectra and an instrument-specific second plurality of spectra from a plurality of samples using said spectroscopic instrument; (c) selecting a set of instrument-specific weight values from a first plurality of weight values, wherein said set includes an instrument-specific weight value for each of said plurality of spectroscopic instruments; (d) performing the following for the selected set of instrument-specific weight values: for each spectroscopic instrument, assigning a respective instrument-specific weight value from the selected set of weight values to each instrument-specific spectrum in said first and said second plurality of spectra, thereby generating an instrument-specific first plurality of weighted spectra and an instrument-specific second plurality of weighted spectra; (e) for the selected set of instrument-specific weight values, determining a corresponding indicator probability value from said first and said second plurality of weighted spectra; (f) repeating steps (c), (d), and (e) until a first predetermined number of different sets of instrument-specific weight values are selected, thereby obtaining a first plurality of indicator probability values; (g) selecting a first target set of instrument-specific weight values as that set of instrument-specific weight values which corresponds to a highest indicator probability value in said first plurality of indicator probability values; and (h) for each spectroscopic instrument, applying an instrument-specific weight value from said first target set to one or more spectra obtained using said spectroscopic instrument.

2. The method of claim 1, wherein the number of indicator probability values in said first plurality of indicator probability values is equal to said first predetermined number.

3. The method of claim 1, wherein said plurality of samples includes samples of only known materials.

4. The method of claim 1, wherein each spectrum in each said first plurality of spectra is obtained from a corresponding first location on a respective one of said plurality of samples, and wherein each spectrum in each said second plurality of spectra is obtained from a corresponding second location on a respective one of said plurality of samples, and wherein said first location is different from said second location for at least one of said plurality of samples.

5. The method of claim 1, wherein each spectrum in an instrument-specific first plurality of spectra has a unique corresponding spectrum in respective instrument-specific second plurality of spectra.

6. The method of claim 1, wherein said plurality of spectroscopic instruments includes two or more of the following: a Raman spectrometer, a mid-infrared spectrometer, an x-ray diffractometer, a fluorescence spectrometer, an energy dispersive x-ray analyzer, and a mass spectrometer.

7. The method of claim 1, wherein step (e) includes: determining a plurality of final probability values by comparing each spectrum in each said second plurality of weighted spectra against each spectrum in each said first plurality of weighted spectra, wherein the number of final probability values in said plurality of final probability values is equal to the number of samples in said plurality of samples; and determining said corresponding indicator probability value for the selected set of instrument-specific weight values using the following equation:

$$\text{Indicator probability value (for the selected set of instrument – specific weight values)} = \sqrt{\frac{\sum_{i=1}^{N}(P_i)^2}{N}},$$

where "N" represents the total number of final probability values for the selected set of instrument-specific weight values, and "$P_i$" refers to the $i^{th}$ final probability value.

8. The method of claim 7, wherein the step of determining said plurality of final probability values includes: obtaining a set of scores based on said comparison of each spectrum in each said second plurality of weighted spectra against each spectrum in each said first plurality of weighted spectra, wherein each score in said set of scores indicates a likelihood of a match between one of said second plurality of weighted spectra and a corresponding one of said first plurality of weighted spectra; calculating a set of relative probability values based on the set of scores; and fusing all relative probability values to thereby produce said plurality of final probability values.

9. The method of claim 1, wherein step (c) includes: selecting a corresponding weight value from said first plurality of weight values for each spectroscopic instrument in such a manner that the total of all weight values in said set of instrument-specific weight values equals to "1".

10. The method of claim 1, wherein step (c) includes one of the following: initially selecting a corresponding predetermined weight value from said first plurality of weight values for each spectroscopic instrument; and initially randomly selecting a corresponding weight value from said first plurality of weight values for each spectroscopic instrument.

11. The method of claim 1, wherein the total number of spectra in each of said first plurality of spectra and said second plurality of spectra is equal to the total number of spectroscopic instruments in said plurality of spectroscopic instruments multiplied by the total number of samples in said plurality of samples.

12. The method of claim 1, further comprising the steps of: (i) generating a second plurality of weight values using weight values in said first target set of instrument-specific weight values; (j) repeating steps (c), (d), and (e) using weight values from said second plurality of weight values instead of weight values from said first, plurality of weight values and until a second predetermined number of different sets of instrument-specific weight values are selected, thereby obtaining a second plurality of indicator probability values; (k) modifying step (g) by selecting a second target set of instrument-specific weight values instead of said first target set, wherein said second target set is that set of instrument-specific weight values which corresponds to a highest indicator probability value in said second plurality of indicator probability values; and (l) for each spectroscopic instrument in step (h), applying an instrument-specific weight value from said second target set instead of said first target set to one or more spectra obtained using said spectroscopic instrument.

13. The method of claim 12, wherein, in step (j), a corresponding weight, value from said second plurality of weight values is selected for each spectroscopic instrument in such a manner that the total of all weight values in said set of instrument-specific weight values equals to "1".

14. The method of claim 12, further comprising enabling a user to perform at least one of the following: step (c); and step (i).

15. A method comprising configuring a processor to perform the following steps: (a) identifying a plurality of spectroscopic instruments; (b) classifying a plurality of samples into a plurality of classes, wherein each class includes one or more of said plurality of samples; (c) for each spectroscopic instrument, obtaining an instrument-specific first plurality of spectra and an instrument-specific second plurality of spectra from samples in one of said plurality of classes using said spectroscopic instrument; (d) selecting a set of instrument-specific weight values from a plurality of weight values, wherein said set includes an instrument-specific weight value for each of said plurality of spectroscopic instruments; (e) performing the following for the selected set of instrument-specific weight values: for each spectroscopic instrument, assigning a respective instrument-specific weight value from the selected set of weight values to each instrument-specific spectrum in said first and said second plurality of spectra, thereby generating an instrument-specific first plurality of weighted spectra and an instrument-specific second plurality of weighted spectra for the samples in said one of said plurality of classes; (f) for the selected set of instrument-specific weight values, determining a corresponding indicator probability value from said first and said second plurality of weighted spectra; (g) repeating steps (d), (e), and (f) until a predetermined number of different sets of instrument-specific weight values are selected, thereby obtaining a plurality of indicator probability values; (h) selecting a target set of instrument-specific weight values as that set of instrument-specific weight values which corresponds to a highest indicator probability value in said plurality of indicator probability values; and (i) for each spectroscopic instrument, applying an instrument-specific weight value from said target set to one or more spectra obtained using said spectroscopic instrument from samples belonging to said one of said plurality of classes.

16. The method of claim 15, wherein step (d) includes: selecting a corresponding weight value from said plurality of weight values for each spectroscopic instrument in such a manner that the total of all weight values in said set of instrument-specific weight values equals to 1.

17. A system comprising: a computer executable program code, which, when executed by a processor, causes said processor to perform the following operations: (a) recognize a plurality of spectroscopic instruments; (b) for each spectroscopic instrument, obtain an instrument-specific first plurality of spectra and an instrument-specific second plurality of spectra from a plurality of samples using said spectroscopic instrument; (c) select a set of instrument-specific weight values from a plurality of weight values, wherein said set includes an instrument-specific weight value for each of said plurality of spectroscopic instruments; (d) perform the following for the selected set of instrument-specific weight values: for each spectroscopic instrument, assign a respective instrument-specific weight value from the selected set of weight values to each instrument-specific spectrum in said first and said second plurality of spectra, thereby generating an instrument-specific first plurality of weighted spectra and an instrument-specific second plurality of weighted spectra; (e) for the selected set of instrument-specific weight values, determine a corresponding indicator probability value from said first and said second plurality of weighted spectra; (f) repeat operations (c), (d), and (e) until a predetermined number of different sets of instrument-specific weight values are selected, thereby obtaining a plurality of indicator probability values; (g) select a target set of instrument-specific weight values as that set of instrument-specific weight values which corresponds to a highest indicator probability value in said plurality of indicator probability values; and (h) for each spectroscopic instrument, apply an instrument-specific weight value from said target set to one or more spectra obtained using said spectroscopic instrument.

18. The system of claim 17, further comprising one or more of the following: said processor configured to execute said program code; and at least one of said plurality of spectroscopic instruments configured to be operationally coupled to said processor.

19. The system of claim 17, wherein said program code, upon execution by said processor, causes said processor to further perform the following: select a corresponding weight value from said plurality of weight values for each spectroscopic instrument in such a manner that the total of all weight values in said set of instrument-specific weight values equals to "1".

20. The system of claim 17, wherein said program code, upon execution by said processor, causes said processor to further perform the following: enable a user to identify to said processor one or more samples in said plurality of samples to be used to obtain said instrument-specific first and second plurality of spectra.

* * * * *